US006966926B2

(12) United States Patent
Mathis

(10) Patent No.: US 6,966,926 B2
(45) Date of Patent: Nov. 22, 2005

(54) MITRAL VALVE THERAPY ASSEMBLY AND METHOD

(75) Inventor: Mark Mathis, Kirkland, WA (US)

(73) Assignee: Cardiac Dimensions, Inc., Kirkland, WA (US)

(*) Notice: Subject to any disclaimer, the term of this patent is extended or adjusted under 35 U.S.C. 154(b) by 259 days.

(21) Appl. No.: 10/659,010

(22) Filed: Sep. 10, 2003

(65) Prior Publication Data
US 2004/0153052 A1 Aug. 5, 2004

Related U.S. Application Data

(62) Division of application No. 09/855,946, filed on May 14, 2001, now Pat. No. 6,676,702.

(51) Int. Cl.$^7$ ............................ A61F 2/24; A61F 11/00
(52) U.S. Cl. ..................... 623/2.36; 623/2.11; 623/904
(58) Field of Search .............................. 623/2.36, 2.37, 623/2.11, 1.11, 903, 904, 1.15; 606/108, 606/191–195, 198, 151, 453; 600/481, 483, 600/485, 37; 128/898

(56) References Cited

U.S. PATENT DOCUMENTS

| | | |
|---|---|---|
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,830,023 A | 5/1989 | de Toledo et al. |
| 5,061,277 A | 10/1991 | Carpentier et al. |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,733,325 A | 3/1998 | Robinson et al. |

(Continued)

FOREIGN PATENT DOCUMENTS

WO    WO 00/44313 A1    8/2000

(Continued)

OTHER PUBLICATIONS

International Search Report for PCT/US02/15233 dated Jun. 5, 2003.

*Primary Examiner*—Alvin J. Stewart
(74) *Attorney, Agent, or Firm*—Wilson, Sonsini, Goodrich and Rosati

(57) ABSTRACT

An assembly for effecting the condition of a mitral valve of a heart includes a mitral valve therapy device, a guide wire, and a guide tube. The mitral valve therapy device is configured to reshape the mitral valve annulus of the heart when placed within the coronary sinus adjacent the mitral valve annulus. The guide wire is configured to be fed into the coronary sinus of the heart adjacent the mitral valve annulus. The guide tube has a distal end, a proximal end, and a lumen extending between the distal end and the proximal end. The guide tube further includes a side port, intermediate the distal and proximal ends which communicates with the lumen. This permits the guide tube to be slidingly received on the guide wire with the guide wire extending from the distal end, through the lumen, and out the side port. In use, the guide tube is slid along the guide wire into the coronary sinus. The mitral valve therapy device is then delivered by the guide tube into the coronary sinus adjacent the mitral valve annulus.

9 Claims, 2 Drawing Sheets

U.S. PATENT DOCUMENTS

| | | | |
|---|---|---|---|
| 5,824,071 A | 10/1998 | Nelson et al. | |
| 5,891,193 A | 4/1999 | Robinson et al. | |
| 5,895,391 A | 4/1999 | Farnholtz | |
| 5,908,404 A | 6/1999 | Elliott | |
| 5,935,161 A | 8/1999 | Robinson et al. | |
| 5,961,545 A | 10/1999 | Lentz et al. | |
| 5,984,944 A | 11/1999 | Forber | |
| 6,027,517 A | 2/2000 | Crocker et al. | |
| 6,071,274 A * | 6/2000 | Thompson et al. | 604/528 |
| 6,071,279 A * | 6/2000 | Whayne et al. | 606/41 |
| 6,076,012 A * | 6/2000 | Swanson et al. | 604/21 |
| 6,077,295 A | 6/2000 | Limon et al. | |
| 6,077,297 A | 6/2000 | Robinson et al. | |
| 6,099,549 A | 8/2000 | Bosma et al. | |
| 6,099,552 A | 8/2000 | Adams | |
| 6,129,755 A | 10/2000 | Mathis et al. | |
| 6,190,406 B1 | 2/2001 | Duerig et al. | |
| 6,210,432 B1 | 4/2001 | Solem et al. | |
| 6,275,730 B1 | 8/2001 | KenKnight et al. | |
| 6,342,067 B1 | 1/2002 | Mathis et al. | |
| 6,352,553 B1 | 3/2002 | van der Burg et al. | |
| 6,352,561 B1 | 3/2002 | Leopold et al. | |
| 6,395,017 B1 | 5/2002 | Dwyer et al. | |
| 6,402,781 B1 | 6/2002 | Langberg et al. | |
| 6,419,696 B1 * | 7/2002 | Ortiz et al. | 623/2.37 |
| 6,442,427 B1 | 8/2002 | Boute et al. | |
| 6,503,271 B2 | 1/2003 | Duerig et al. | |
| 6,537,314 B2 * | 3/2003 | Langberg et al. | 623/2.36 |
| 6,569,198 B1 | 5/2003 | Wilson et al. | |
| 6,589,208 B2 | 7/2003 | Ewers et al. | |
| 6,602,288 B1 | 8/2003 | Cosgrove et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,656,221 B2 | 12/2003 | Taylor et al. | |
| 6,676,702 B2 * | 1/2004 | Mathis | 623/2.36 |
| 6,716,158 B2 | 4/2004 | Raman et al. | |
| 6,718,985 B2 | 4/2004 | Hlavka et al. | |
| 6,723,038 B1 | 4/2004 | Schroeder et al. | |
| 6,793,673 B2 * | 9/2004 | Kowalsky et al. | 623/2.36 |
| 6,800,090 B2 * | 10/2004 | Alferness et al. | 623/2.36 |
| 2001/0018611 A1 | 8/2001 | Solem et al. | |
| 2001/0044568 A1 | 11/2001 | Langberg et al. | |
| 2001/0049558 A1 | 12/2001 | Liddicoat et al. | |
| 2002/0016628 A1 | 2/2002 | Langberg et al. | |
| 2002/0035361 A1 | 3/2002 | Houser et al. | |
| 2002/0042621 A1 | 4/2002 | Liddicoat et al. | |
| 2002/0042651 A1 | 4/2002 | Liddicoat et al. | |
| 2002/0049468 A1 | 4/2002 | Streeter et al. | |
| 2002/0055774 A1 | 5/2002 | Liddicoat | |
| 2002/0065554 A1 | 5/2002 | Streeter | |
| 2002/0087173 A1 | 7/2002 | Alferness et al. | |
| 2002/0095167 A1 | 7/2002 | Liddicoat et al. | |
| 2002/0103532 A1 | 8/2002 | Langberg et al. | |
| 2002/0103533 A1 | 8/2002 | Langberg et al. | |
| 2002/0138044 A1 | 9/2002 | Streeter et al. | |
| 2002/0151961 A1 | 10/2002 | Lashinski et al. | |
| 2002/0169502 A1 | 11/2002 | Mathis | |
| 2002/0169504 A1 * | 11/2002 | Alferness et al. | 623/2.36 |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2003/0018358 A1 | 1/2003 | Saadat | |
| 2003/0069636 A1 | 4/2003 | Solem et al. | |
| 2003/0078465 A1 | 4/2003 | Pai et al. | |
| 2003/0078654 A1 | 4/2003 | Taylor et al. | |
| 2003/0083538 A1 | 5/2003 | Adams et al. | |
| 2003/0088305 A1 | 5/2003 | Van Schie et al. | |
| 2003/0105520 A1 | 6/2003 | Alferness et al. | |
| 2003/0130730 A1 | 7/2003 | Cohn et al. | |
| 2003/0130731 A1 | 7/2003 | Vidlund et al. | |
| 2003/0135267 A1 | 7/2003 | Solem et al. | |
| 2003/0144697 A1 | 7/2003 | Mathis et al. | |
| 2003/0171776 A1 | 9/2003 | Adams et al. | |
| 2003/0171806 A1 | 9/2003 | Mathis et al. | |
| 2003/0212453 A1 | 11/2003 | Mathis et al. | |
| 2004/0019377 A1 | 1/2004 | Taylor et al. | |
| 2004/0039443 A1 | 2/2004 | Solem et al. | |
| 2004/0073302 A1 | 4/2004 | Rourke et al. | |
| 2004/0249452 A1 * | 12/2004 | Adams et al. | 623/2.36 |
| 2005/0027353 A1 * | 2/2005 | Alferness et al. | 623/2.11 |
| 2005/0033419 A1 * | 2/2005 | Alferness et al. | 623/2.11 |
| 2005/0038507 A1 * | 2/2005 | Alferness et al. | 623/2.11 |

FOREIGN PATENT DOCUMENTS

| | | |
|---|---|---|
| WO | PCT-WO 00/60995 | 10/2000 |
| WO | WO 01/00111 A1 | 1/2001 |
| WO | WO 01/50985 A1 | 7/2001 |
| WO | PCT-WO 01/54618 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/62263 A2 | 8/2002 |
| WO | WO 02/62270 A1 | 8/2002 |
| WO | WO-02/62408 A2 | 8/2002 |
| WO | WO 02/76284 A2 | 10/2002 |
| WO | WO 02/78576 A2 | 10/2002 |
| WO | WO 02/96275 A2 | 12/2002 |
| WO | WO-03/15611 A2 | 2/2003 |
| WO | WO-03/49647 A1 | 6/2003 |
| WO | WO-03/59198 A2 | 7/2003 |

* cited by examiner

MITRAL VALVE THERAPY ASSEMBLY AND METHOD

This is a divisional of the prior application Ser. No. 09/855,946, filed May 14, 2001 now U.S. Pat. No. 6,676,702, the benefit of the filing date of which is hereby claimed under 35 USC 120.

FIELD OF THE INVENTION

The present invention generally relates to a system and method for treating a deformed heart valve. The present invention more particularly relates to a system and method for delivering a mitral valve therapy device into the coronary sinus of a heart to treat mitral valve dilation.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Unfortunately, the human anatomy does impose some obstacles to this recently proposed procedure for treating mitral regurgitation. More specifically, the human heart includes a coronary artery which descends from the aorta. One branch of the coronary artery is the circumflex artery which, in turn, includes the left marginal branch of the circumflex artery. As used herein, the term "circumflex artery" is taken to include the circumflex artery itself or any branch therefrom. The circumflex artery extends distally generally along the coronary sinus but at a point proximal to the coronary artery, it passes under the coronary sinus. The circumflex artery supports blood flow important to the viability of the heart. Hence, reduction in this blood flow must be avoided. As a result, a device placed in the coronary sinus must not be permitted to extend within the coronary sinus beyond the crossover point of the circumflex artery and the coronary sinus to avoid constriction of the circumflex artery. This contemplates the need to know the location of the circumflex artery and coronary sinus crossover point. It also contemplates accurate positioning of the device within the coronary sinus to assure that the device does not extend over the circumflex artery.

The present invention addresses these issues. The present invention provides a therapy system and procedure which enables accurate positioning of the therapy device. This enables effective treatment while also avoiding the crossover of the circumflex artery with the coronary sinus. Further, the present invention enables the positioning of the device with relative ease.

SUMMARY OF THE INVENTION

The present invention provides an assembly for effecting the condition of a mitral valve of a heart. The assembly includes a mitral valve therapy device configured to reshape the mitral valve annulus of the heart when placed within the coronary sinus adjacent the mitral valve annulus, a guide wire configured to be fed into the coronary sinus of the heart adjacent the mitral valve annulus, and a guide tube having a distal end, a proximal end, and a lumen extending between the distal end and the proximal end, the guide tube further including a side port, intermediate the distal end and the proximal end and communicating with the lumen, to permit the guide tube to be slidingly received on the guide wire with the guide wire extending from the distal end, through the lumen, and out the side port. As a result, the guide tube is slidable along the guide wire to a position adjacent the mitral valve annulus within the coronary sinus and the mitral valve therapy device is guidable within the guide tube for placement in the coronary sinus adjacent the mitral valve annulus.

The present invention further provides a method of deploying a mitral valve therapy device within the coronary sinus of a heart adjacent the mitral valve annulus. The method includes the steps of providing an elongated flexible guide wire having a cross sectional dimension, feeding the guide wire into the coronary sinus of the heart, providing an elongated flexible guide tube having a proximal end, a distal end, a lumen, and a side port communicating with the lumen, and feeding the guide tube into the coronary sinus of the heart with the guide wire extending through the lumen from the distal end to and through the side port. The method further includes the steps of providing a mitral valve therapy device configured to be slidingly received within the lumen of the guide tube, the device including a proximal end, providing a flexible elongated introducer configured to be slidingly received within the lumen of the guide tube, the introducer having a distal end, placing the device into the guide tube lumen, placing the introducer into the guide tube lumen, engaging the distal end of the introducer with the proximal end of the device, pushing the device with the introducer in a distal direction within the guide tube lumen until the device is at least partially encircling the mitral valve within the coronary sinus of the heart, and releasing the device from the guide tube into the coronary sinus of the heart adjacent to the mitral valve annulus.

The guide wire may be visible under X ray fluoroscopy and the method may include the further steps of inserting a second wire into the circumflex artery of the heart, the second wire being visible under X ray fluoroscopy, subjecting the heart to X ray fluoroscopic examination to visualize the crossover point of the guide wire and the second wire, and releasing the mitral valve annulus therapy device within the coronary sinus in a position such that the device is proximal to the crossover point of the guide wire and the second wire.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, and the several figures of which like reference numerals identify identical elements, and wherein:

DETAILED DESCRIPTION OF THE INVENTION

Figure 1:
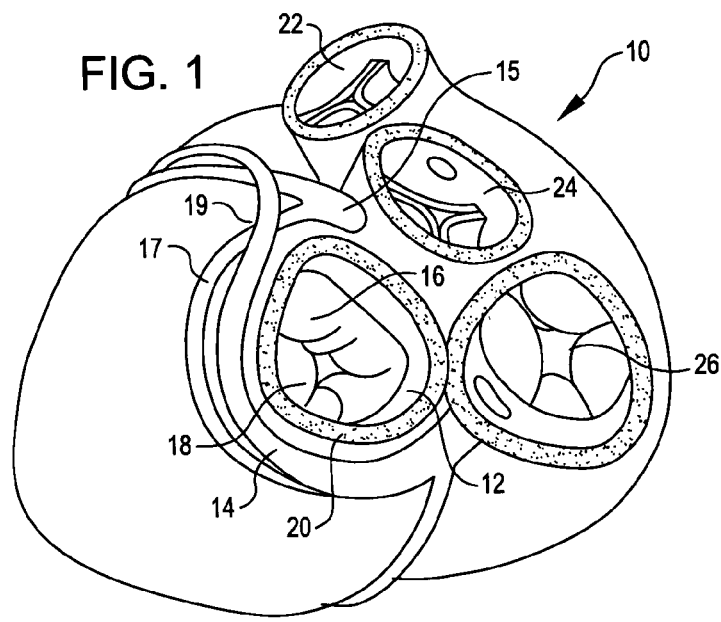
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Of particular importance is the physiological relationship of the coronary sinus 14 and the circumflex artery 17. The circumflex artery 17 branches from the coronary artery 15 and supplies blood flow to critical tissue of the heart 10. The circumflex artery passes beneath the coronary sinus 14 at a crossover point 19. It is one aspect of the present invention to avoid constriction of blood flow through the circumflex artery 17 when a mitral valve therapy device is deployed in the coronary sinus 14.

Figure 2:
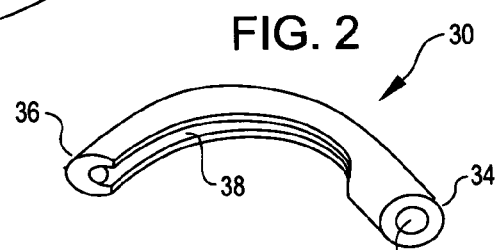
FIG. 2 is a perspective view of a mitral valve annulus constricting device which may be utilized in accordance with an embodiment of the present invention.

FIG. 2 shows a mitral valve therapy device 30 embodying the present invention. As may be noted in FIG. 2, the device is elongated and has an arched configuration to at least partially encircle the mitral valve 12 adjacent to the mitral valve annulus 20 when implanted in the coronary sinus 14. The device 30 has an unstressed preformed arched radius smaller than the radius of the dilated mitral valve annulus 20. This causes the device 30 to constrict the mitral valve annulus and impart an inward, generally radial force on the mitral valve annulus 20 when implanted in the coronary sinus of the heart. This force reshapes and returns the mitral valve annulus 20 to its original or substantially original geometry to permit the cusps 16 and 18 to more fully come together for sealing the left atrium during left ventricular contraction.

The device 30 has a cross section dimension to be received by the coronary sinus. It is preferably formed of a resilient material permitting the device to be straightened and/or bent for being advanced into the coronary sinus. After being positioned within the coronary sinus, the device is permitted to assume its preformed arched configuration to act upon the mitral valve annulus as previously described. To that end, the device may be formed of, for example, Nitinol, a nickel titanium alloy, well known in the art. This material, as is well known, is capable of being preformed but manipulated to be straight or partially bent while having sufficient memory to return to its preformed configuration. Stainless steel is also among the materials which may be used in forming the device 30. In order to be received within the coronary sinus, the device may have a cross sectional dimension of, for example, on the order of four or five french.

With continued reference to FIG. 2, the device 30 has a distal end 34 and a proximal end 36. Between the distal end 34 and proximal end 36 the device further includes a channel 38 which is aligned with a bore 40 extending through the distal end 34. As will be seen subsequently, the bore 40 permits the device to be slidingly received by a guide wire during deployment of the device 30. The guide wire, during deployment, is confined within the channel 38.

Figure 3:
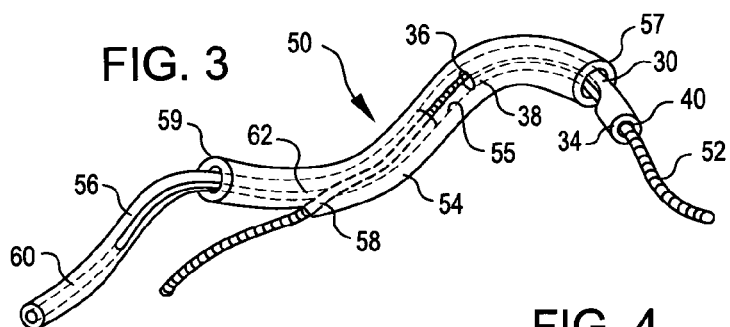
FIG. 3 is a perspective view of an assembly for treating a mitral valve in accordance with a preferred embodiment of the present invention.

FIG. 3 illustrates an assembly 50 for deploying or implanting the mitral valve therapy device 30. The assembly 50 includes a guide wire 52, a guide tube 54, and an elongated introducer 56.

The guide wire 52 is preferably an elongated coil. It has an outer dimension to permit the guide wire 52 to be passed through the bore 40 of the device 30. This enables the device 30 to be slidingly received on the guide wire 52 with the guide wire confined within the channel 38 of the device 30.

The guide tube 54 is elongated and formed of a flexible biocompatible material. It includes an inner lumen 55 extending between a distal end 57 and a proximal end 59 permitting the device 30 and the introducer 56 to be received therein. The guide tube 54 further includes a side port 58 between the distal end 57 and the proximal end 59. The side port 58 communicates with the lumen 55 to permit the guide tube 54 to be received on the guide wire 52. More specifically, the guide tube 54 is slidingly received on the guide wire 52 with the guide wire extending through the lumen from the distal end 57 to and through the side port 58. This permits the guide tube 54 to be advanced along the guide wire 52 during implant of the device 30.

The introducer 56 preferably takes the form of an elongated tube having an inner channel 60 and a slot 62 at its distal end dimensioned to be received by and slid onto the guide wire 52. This enables the introducer 56 to be slid onto the guide wire 52 and to engage the proximal end of the device 30 during deployment of the device.

Figure 6:
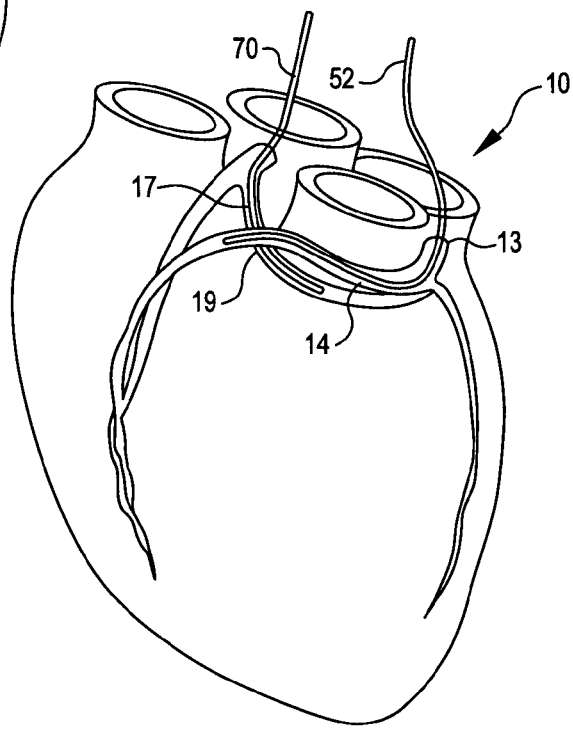
FIG. 6 is another view of a human heart illustrating the method of determining the crossover point of the circumflex artery and the coronary sinus in accordance with the present invention.

As previously mentioned, the circumflex artery 17 passes under the coronary sinus 14. When the device 30 is deployed, it should not be permitted to exert a force from the coronary sinus against the circumflex artery. Hence, in accordance with one embodiment of the present invention, the device is implanted within the coronary sinus at a position whereby the distal end 34 of the device 30 is proximal to the crossover point of the circumflex artery and the coronary sinus. This requires determination of the crossover point. FIG. 6 illustrates how such a determination may be made in accordance with the present invention.

An elongated member, such as an elongated wire or coil wire 70 is inserted into the circumflex artery 17. The wire 70 may be formed of a material visible under X ray fluoroscopy or be of other material having a coating which is visible under X ray fluoroscopy. Next, another wire which may be the guide wire 52 is inserted into the coronary sinus 14 by way of the ostium of coronary sinus 13. Again, the wire 52 is preferably of a material visible under X ray fluoroscopy or of another material having a coating which is visible under X ray fluoroscopy. Preferably, the wires 52 and 70 are elongated coils formed of stainless steel.

The heart 10 or at least that portion of the heart 10 where the circumflex artery passes under the coronary sinus is subjected to X ray fluoroscopy. X ray fluoroscopy is well known in the art. The crossover point 19 where the wires 52 and 70 cross and hence where the circumflex artery and coronary sinus cross may then be readily observed by X ray fluoroscopic examination. This locates the crossover point 19 which is to be distal to the distal end 34 of the device 30 when the device 30 is positioned within the coronary sinus.

Once the crossover point 19 has been determined, the device 30 may be deployed. During the deployment of the device, the first wire 70 may be left in the circumflex artery to permit continuous X ray fluoroscopic examination or later X ray fluoroscopic examination to confirm proper device positioning.

Figure 4:
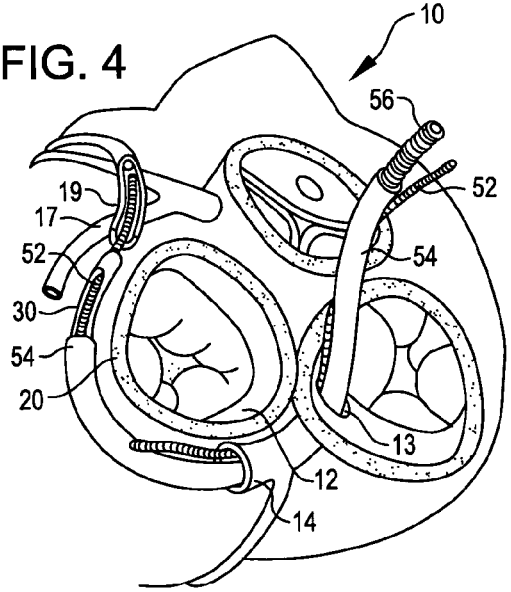
FIG. 4 is another superior view of a human heart illustrating deployment of a mitral valve therapy device in accordance with the preferred embodiment of the present invention.

FIG. 4 shows how the assembly 50 may be used to implant the device 30. Presumably the guide wire 52 has already been positioned in the coronary sinus 14 to support the determination of the circumflex artery and coronary sinus crossover point as described above. As also described above, wire 70 may also be left in the heart at this time.

Next, the device 30 is threaded onto the guide wire 52 and the guide tube 54 is slidingly mounted on the guide wire 52 as shown in FIG. 3. The device 30 is then slid into the distal end 57 of the guide tube 54. The guide tube 54 is then advanced into the heart. The guide tube is advanced on the guide wire 52. The guide wire hence guides the guide tube 54 into the coronary sinus where the device is to be implanted.

When the guide tube 54 is positioned in the coronary sinus, the introducer 56 is then advanced into the guide tube 54 and over the guide wire 52. The distal end of the introducer 56 engages the proximal end 36 of the device 30.

With the distal end of the introducer 56 engaging the proximal end 36 of the device 30, the guide tube may be slightly retracted and the device may then be pushed by the introducer 56 out of the guide tube 54 and into the coronary sinus 14 while remaining on the guide wire 52.

When the device is positioned within the coronary sinus 14 with its distal end proximal to the crossover point 19 and its position is confirmed by X ray fluoroscopy, the introducer may be removed. Then, the guide tube 54 may also be retracted leaving the device in place but still on the guide wire 52. The performance of the device 30 may now be evaluated.

Figure 5:
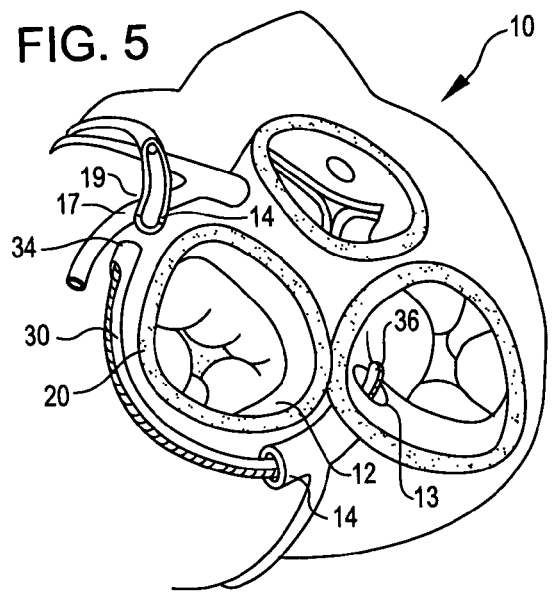
FIG. 5 is another superior view of a human heart illustrating an implanted mitral valve therapy device embodying the present invention.

Once the device satisfies the requirements of the procedure, the guide wire 52, and the wire 70 if still within the heart, may be removed. This leaves the device 30 in its proper position as illustrated in FIG. 5. Here it may be seen that the device 30 partially encircles the mitral valve 12 within the coronary sinus 14 and adjacent to the mitral valve annulus. The distal end 34 of the device 30 is proximal to the crossover point 19. The proximal end 36 of the device protrudes slightly into the right atrium (not shown) through the ostium of coronary sinus 13.

Figure 7:
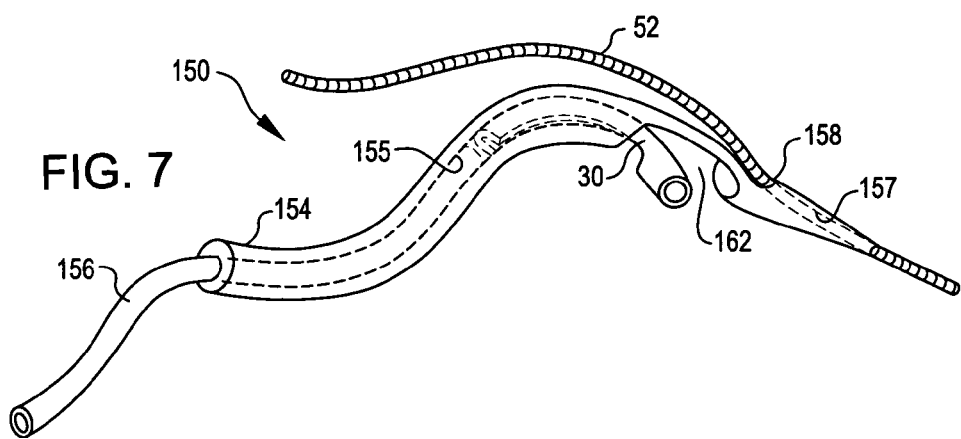
FIG. 7 is a perspective view of another assembly embodying the present invention for treating a mitral valve.

FIG. 7 shows another assembly 150 for treating a mitral valve embodying the present invention. The assembly may utilize the same device 30 and guide wire 52 as previously described. Here, however, a different guide tube 154 and introducer 156 are employed. The guide tube includes a bore 157 extending from the distal end of the guide tube to a side port 158. The bore receives the guide wire 52 as shown to permit the guide tube 154 to slide on the guide wire 52. The guide tube 154 further has a lumen 155 for receiving the device 30 and the introducer. A delivery slot 162 is proximal to the side port 158 and communicates with the lumen 155. Hence, when the guide tube is within the coronary sinus, the introducer may push the device through the lumen 155 and out the delivery slot 162 into the coronary sinus for deployment. As will be appreciated by those skilled in the art, the lumen 155 and bore 157 may communicate to form a single lumen. The side port 158 may then communicate with the single lumen in the same manner as shown in FIG. 3.

The introducer 156 need not be received by the guide wire 52 in this embodiment. Hence, the introducer 156 need not be slotted as shown in FIG. 3 and preferably takes the form of an elongated coil.

As can thus be seen from the foregoing, the present invention provides a new and improved assembly and method for treating mitral regurgitation. The device may be rapidly deployed with only percutaneous techniques. Further, the mitral valve therapy device may be implanted in a manner which avoids the crossover point of the circumflex artery and coronary sinus. Lastly, the effectiveness of the therapy may be immediately deduced during the implant procedure.

While particular embodiments of the present invention have been shown and described, modifications may be made, and it is therefore intended in the appended claims to cover all such changes and modifications which fall within the true spirit and scope of the invention.

What is claimed:

1. A method of deploying a mitral valve therapy device within the coronary sinus of a heart adjacent the mitral valve annulus, the method including the steps of:
    A. providing an elongated flexible guide wire having a cross sectional dimension;
    B. feeding guide wire into the coronary sinus of the heart;
    C. providing an elongated flexible guide tube having a proximal end, a distal end, a lumen, and a side port communicating with the lumen;
    D. feeding the guide tube into the coronary sinus of the heart with the guide wire extending through the lumen from the distal end to and through the side port;
    E. providing a mitral valve therapy device configured to be slidingly received within the lumen of the guide tube, the device including a proximal end;
    F. providing a flexible elongated introducer configured to be slidingly received within the lumen of the guide tube, the introducer having a distal end;
    G. placing the device into the guide tube lumen;
    H. placing the introducer into the guide tube lumen;
    I. engaging the distal end of the introducer with the proximal end of the device;
    J. pushing the device with the introducer in a distal direction within the guide tube lumen until the device is at least partially encircling the mitral valve within the coronary sinus of the heart; and
    K. releasing the device from the guide tube into the coronary sinus of the heart adjacent to the mitral valve annulus.

2. The method of claim 1 wherein the step of placing the device into the guide tube lumen includes the step of placing the device on the guide wire.

3. The method of claim 1 wherein the step of placing the introducer into the guide tube lumen includes the step of placing the introducer on the guide wire.

4. The method of claim 1 including the further step of providing a delivery slot in the guide tube proximal to the side port and communicating with the lumen, and wherein the releasing step includes the step of advancing the device from the lumen through the delivery slot and into the coronary sinus.

5. The method of claim 1 wherein the releasing step includes the step of releasing the device from the distal end of the guide tube.

6. The method of claim 1 wherein the step of placing the device into the guide tube lumen includes placing the device on the guide wire and wherein the step of releasing the device includes releasing the device from the distal end of the guide tube.

7. The method of claim 6 including the further step of testing the effectiveness of the device while the device is on the guide wire.

8. The method of claim 1 including the further step of withdrawing the introducer, the guide tube, and the guide wire from the coronary sinus.

9. The method of claim 1 wherein the guide wire is visible under X ray fluoroscopy and wherein the method includes the further steps of:

inserting a second wire into the circumflex artery of the heart, the second wire being visible under X ray fluoroscopy;

subjecting the heart to X ray fluoroscopic examination to visualize the crossover point of the guide wire and the second wire; and releasing the mitral valve annulus therapy device within the coronary sinus in a position such that the device is proximal to the crossover point of the guide wire and the second wire.

\* \* \* \* \*